(12) United States Patent
Thistle

(10) Patent No.: US 7,530,994 B2
(45) Date of Patent: May 12, 2009

(54) NON-POROUS GRAFT WITH FASTENING ELEMENTS

(75) Inventor: Robert C. Thistle, Bridgewater, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 460 days.

(21) Appl. No.: 10/748,610

(22) Filed: Dec. 30, 2003

(65) Prior Publication Data

US 2005/0149165 A1 Jul. 7, 2005

(51) Int. Cl.
*A61F 2/06* (2006.01)
(52) U.S. Cl. ........................................ 623/1.13
(58) Field of Classification Search .................. None
See application file for complete search history.

(56) References Cited

U.S. PATENT DOCUMENTS

| | | | |
|---|---|---|---|
| 5,123,917 A | 6/1992 | Lee | |
| 5,152,782 A | 10/1992 | Kowligi et al. | |
| 5,254,127 A | 10/1993 | Wholey et al. | |
| 5,387,236 A | 2/1995 | Noishiki et al. | |
| 5,527,353 A * | 6/1996 | Schmitt | 623/1.44 |
| 5,549,860 A | 8/1996 | Charlesworth et al. | |
| 5,628,788 A | 5/1997 | Pinchuk | |
| 5,665,114 A | 9/1997 | Weadock et al. | |
| 5,674,241 A | 10/1997 | Bley et al. | |
| 5,693,085 A | 12/1997 | Buirge et al. | |
| 5,700,285 A | 12/1997 | Myers et al. | |
| 5,723,004 A | 3/1998 | Dereume et al. | |
| 5,735,892 A | 4/1998 | Myers et al. | |
| 5,749,880 A | 5/1998 | Banas et al. | |
| 5,800,512 A | 9/1998 | Lentz et al. | |
| 5,843,166 A | 12/1998 | Lentz et al. | |
| 5,876,432 A | 3/1999 | Lau et al. | |
| 5,891,193 A * | 4/1999 | Robinson et al. | 128/898 |
| 5,916,264 A | 6/1999 | Von Oepen et al. | |
| 5,925,075 A | 7/1999 | Myers et al. | |
| 5,928,279 A | 7/1999 | Shannon et al. | |
| 5,948,018 A | 9/1999 | Dereume et al. | |
| 5,961,545 A | 10/1999 | Lentz et al. | |
| 5,976,192 A | 11/1999 | McIntyre et al. | |
| 6,001,125 A | 12/1999 | Golds et al. | |
| 6,139,573 A | 10/2000 | Sogard et al. | |

(Continued)

FOREIGN PATENT DOCUMENTS

EP 1 208 817 A2 5/2002

(Continued)

OTHER PUBLICATIONS

International Search Report related to PCT/US2004/040556 with an international filing date of Jun. 12, 2004.

*Primary Examiner*—Corrine McDermott
*Assistant Examiner*—Christopher D Prone
(74) *Attorney, Agent, or Firm*—RatnerPrestia

(57) ABSTRACT

A graft is provided that is adapted to be secured to a stent surrounding the graft. The graft includes an inner layer of a non-porous material, and an outer layer of material laminated to the inner layer. The graft further includes a plurality of fastening elements adapted to be secured to a stent surrounding the graft. An underside of each fastening element is fixed between the inner layer and the outer layer.

17 Claims, 2 Drawing Sheets

U.S. PATENT DOCUMENTS

| | | |
|---|---|---|
| 6,156,064 A | 12/2000 | Chouinard |
| 6,165,212 A | 12/2000 | Dereume et al. |
| 6,187,054 B1 | 2/2001 | Colone et al. |
| 6,203,735 B1 | 3/2001 | Edwin et al. |
| 6,214,039 B1 | 4/2001 | Banas et al. |
| 6,309,343 B1 | 10/2001 | Lentz et al. |
| 6,322,585 B1 * | 11/2001 | Khosravi et al. ............ 623/1.11 |
| 6,331,191 B1 | 12/2001 | Chobotov |
| 6,357,104 B1 | 3/2002 | Myers |
| 6,364,903 B2 | 4/2002 | Tseng et al. |
| 6,368,347 B1 | 4/2002 | Maini et al. |
| 6,395,019 B2 * | 5/2002 | Chobotov .................. 623/1.13 |
| 6,398,803 B1 | 6/2002 | Layne et al. |
| 6,428,571 B1 | 8/2002 | Lentz et al. |
| 6,440,166 B1 | 8/2002 | Kolluri |
| 6,443,981 B1 | 9/2002 | Colone et al. |
| 6,451,047 B2 | 9/2002 | McCrea et al. |
| 6,488,701 B1 | 12/2002 | Nolting et al. |
| 6,514,283 B2 | 2/2003 | DiMatteo et al. |
| 6,517,570 B1 | 2/2003 | Lau et al. |
| 6,517,571 B1 | 2/2003 | Brauker et al. |
| 6,524,334 B1 | 2/2003 | Thompson |
| 6,540,773 B2 | 4/2003 | Dong |
| 6,540,780 B1 | 4/2003 | Zilla et al. |
| 6,547,815 B2 | 4/2003 | Myers |
| 6,554,855 B1 | 4/2003 | Dong |
| 6,626,939 B1 | 9/2003 | Burnside et al. |
| 2002/0026231 A1 | 2/2002 | Shannon et al. |
| 2003/0017775 A1 | 1/2003 | Sowinski et al. |
| 2003/0060871 A1 | 3/2003 | Hill et al. |
| 2003/0114917 A1 | 6/2003 | Holloway et al. |
| 2003/0116260 A1 | 6/2003 | Chobotov et al. |
| 2003/0204241 A1 | 10/2003 | Dong |

FOREIGN PATENT DOCUMENTS

| | | |
|---|---|---|
| FR | 2 833 153 A1 | 6/2003 |

* cited by examiner

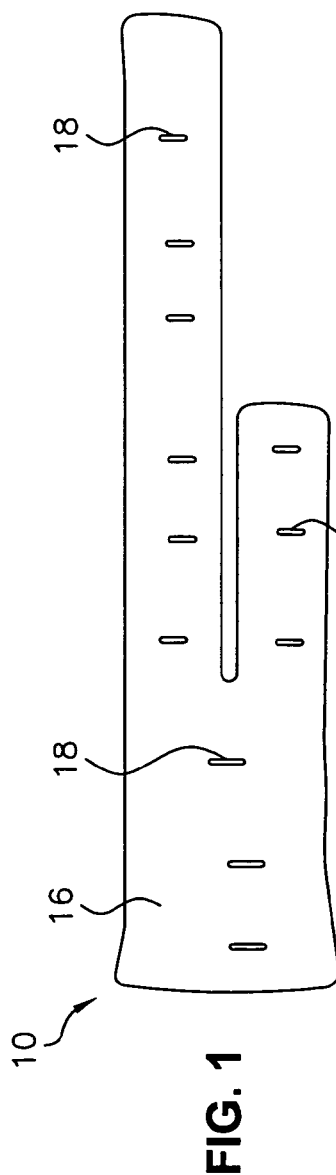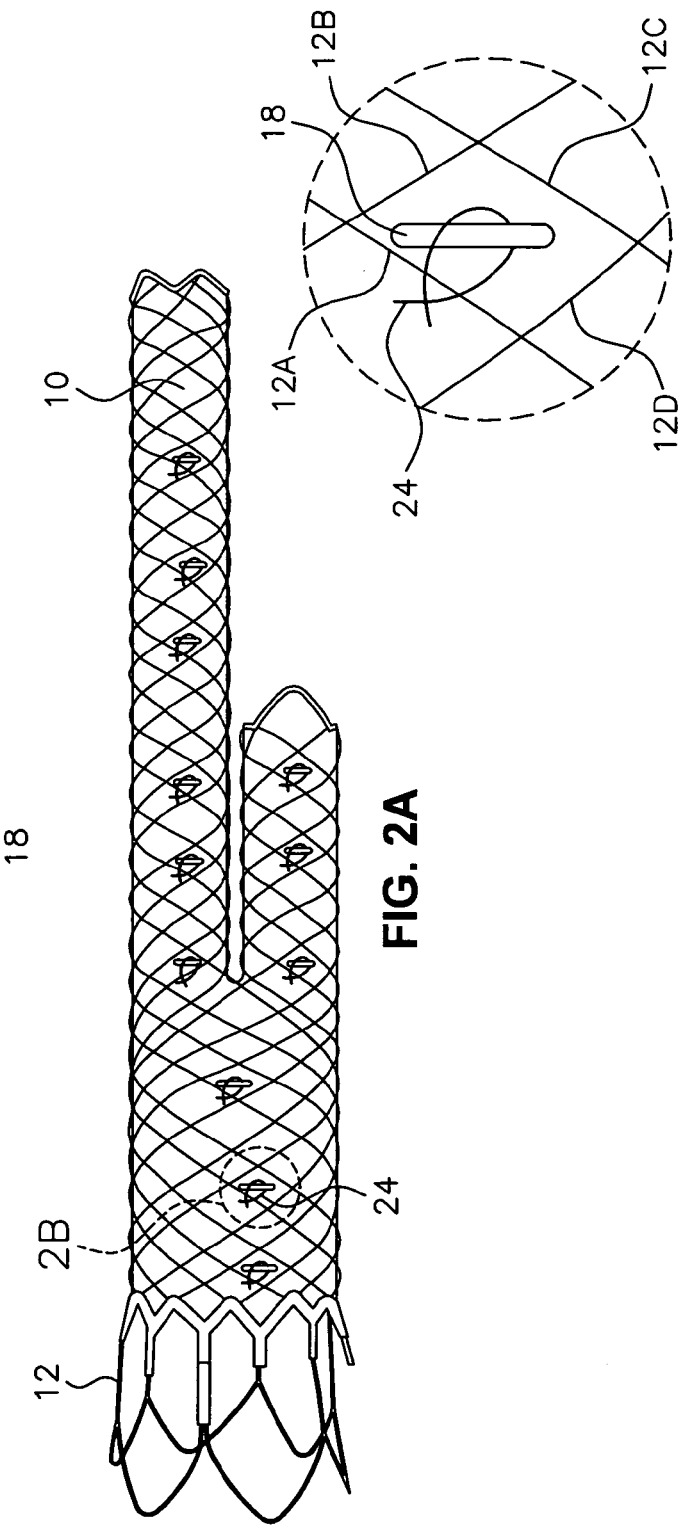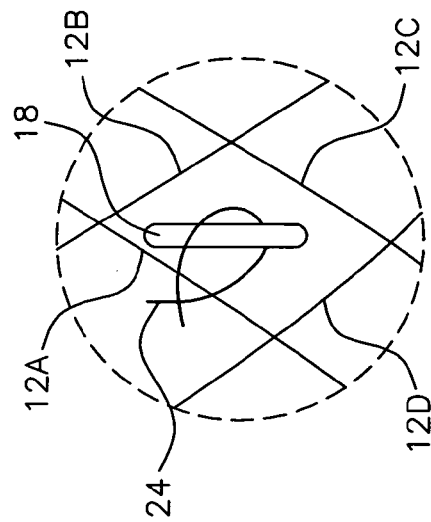

NON-POROUS GRAFT WITH FASTENING ELEMENTS

FIELD OF THE INVENTION

The present invention relates to a graft for use with a stent in body lumens. More specifically, the present invention relates to a graft adapted to be secured to a stent surrounding the graft.

BACKGROUND OF THE INVENTION

A graft is typically used in conjunction with a stent to provide a prosthetic intraluminal wall, e.g., in the case of a stenosis or aneurysm, to provide an unobstructed conduit for blood in the area of the stenosis or aneurysm. A stent-graft may be endoluminally deployed in a body lumen, a blood vessel for example, at the site of a stenosis or aneurysm by so-called "minimally invasive techniques" in which the stent-graft is compressed radially inwards and is delivered by a catheter to the site where it is required, through the patient's skin, or by a "cut down" technique at a location where the blood vessel concerned is accessible. When the stent-graft is positioned at the correct location, the stent-graft is caused or allowed to re-expand is to a predetermined diameter in the vessel.

Some early stent-grafts were manufactured by bonding the graft material to the stent frame with an adhesive, e.g., Corethane®. However, such an adhesive alone may not be sufficient to secure the graft to the stent during loading, as the graft material may peel away (i.e., separate) from the stent. Suture ties may also be utilized to fix the graft to the stent. However, suture attachment of the graft to the stent may create holes throughout the graft resulting in porosity which may be undesirable. For these and other reasons, improvements in securing a graft to a stent may have significant utility as compared to prior stent-graft combinations.

SUMMARY OF THE INVENTION

According to one aspect of this invention, a graft is adapted to be secured to a stent surrounding the graft in a novel way. The graft, typically tubular, includes an inner layer of a non-porous material, and an outer layer typically of knitted, woven, or braided material laminated to the inner layer. The graft further includes a plurality of fastening elements adapted to be secured to a stent surrounding the graft. An underside of each fastening element is fixed between the inner layer and the outer layer of the graft.

According to another aspect of this invention, a method of making a non-porous graft, and a stent-graft using that graft, is provided. A plurality of fastening elements are secured to an outer layer typically of knitted, woven, or braided material along a length of the outer layer, wherein the fastening elements extend outwardly from the outer layer. An inner layer of non-porous material is placed within the outer layer such that an underside of each fastening element is positioned between the inner layer and the outer layer. The outer layer is laminated to the inner layer to form the non-porous graft, which is then placed within a surrounding graft. The fastening elements are then secured to the stent.

The fastening elements may comprise loops which extend through openings in the stent and are adapted to secure the graft to the stent by a mating element, such as a linear element (or suture) which passes through each of these loops and secures them, optionally with a knot, to a structural part of the stent.

The resultant stent-graft may be used to provide a fluid passage through a body lumen. It may also be adapted for endoluminal placement.

BRIEF DESCRIPTION OF THE DRAWINGS

FIG. 1 is a plan view of a tubular graft including a plurality of fastening elements in accordance with the present invention;

FIG. 2A is a plan view of a non-porous tubular stent-graft including a plurality of fastening elements secured to a stent by a plurality of looped locking elements in accordance with the present invention;

FIG. 2B is a detail view of a fastening element secured to an element of the stent by a looped locking element illustrated in FIG. 2A;

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims without departing from the invention.

Figure 3:
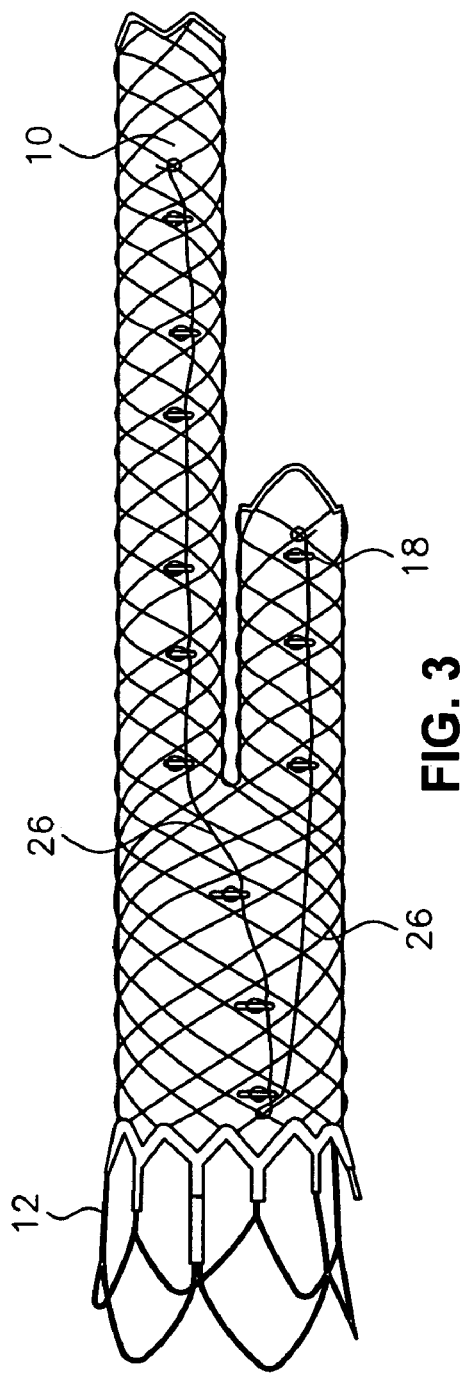
FIG. 3 is a plan view of a non-porous tubular stent-graft including a plurality of fastening elements secured to a stent by a linear locking element in accordance with the present invention.
Figure 4:
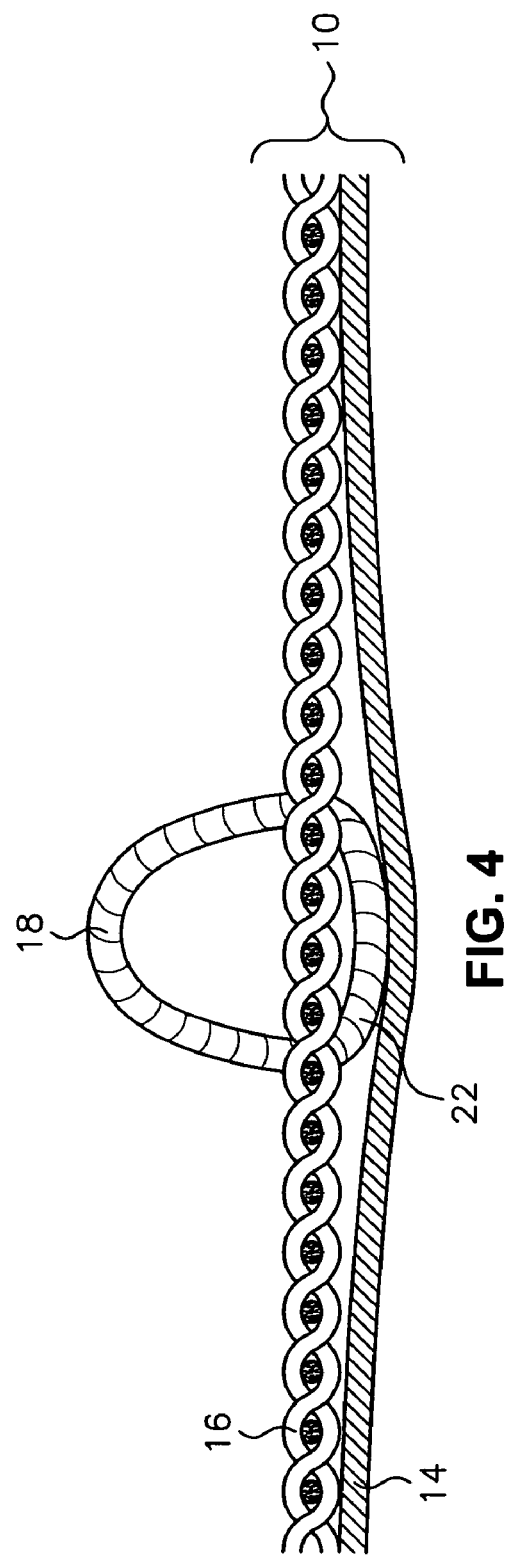
FIG. 4 is a cross-sectional view of the non-porous tubular graft of FIG. 1, illustrating an outer layer laminated to an inner layer and a fastening element fixed between the layers.

Referring specifically to FIGS. 1-4, there is shown a tubular graft 10 (best seen in FIG. 1) adapted to be secured to a stent 12 surrounding graft 10 in different ways (as illustrated in FIGS. 2A and 3). Stent 12 includes a plurality of structural members, four of which are identified in FIG. 2B as 12A, B, C, and D. FIG. 4 is a cross-sectional expanded view of graft 10 illustrating an inner layer 14 of a non-porous material, and an outer layer 16 of knitted, woven, or braided material laminated to inner layer 14. Graft 10 further includes a plurality of fastening elements 18 (only one of which is seen in FIG. 4) adapted to be secured on an outer surface 20 of stent 12 surrounding graft 10. An underside 22 of each fastening element 18 is fixed between inner layer 14 and outer layer 16. A plurality of fastening elements 18 may be distributed lengthwise along the length of graft 10, as shown in FIGS. 1, 2A, and 3, and/or circumferentially about graft 10 (not shown).

Fastening elements 18 extend outwardly from outer layer 16, as illustrated in FIG. 4. Non-porous inner layer 14 reduces or minimizes the porosity of graft 10, thus compensating for any such porosity in outer layer 16. Fastening elements 18 are retained between outer layer 16, which is laminated to inner layer 14, sealing underside 22 of each fastening element 18 between outer layer 16 and inner layer 14. The finished assembly remains non-porous, resulting in a non-porous graft 10.

Referring to FIG. 2A, the exemplary configuration illustrates graft 10 attached to an inside surface of stent 12 with fastening elements 18 projecting through stent 12 and a plurality of looped locking elements 24, shown in greater detail in FIG. 2B, securing fastening elements 18 to stent 12, thereby securing graft 10 to stent 12. In this embodiment, each locking element 24 is knotted around both a fastening element 18 and an element or structural component of stent 12 to attach graft 10 to stent 12. FIG. 2B is a detail view of a fastening element 18 secured to an element 12A of stent 12 by a looped locking element 24. Alternatively, a particular fastening element 18 may be secured to any one or more of elements 12B, 12C, or 12D of stent 12 by looped locking element 24.

As shown in FIG. 2B, fastening elements 18 may comprise D-shaped loops, the flat side of which is trapped between inner layer 14 and outer layer 16, with the remainder of the loop projecting outwardly through outer layer 16.

Similar to FIG. 2A, the exemplary configuration represented in FIG. 3 illustrates graft 10 attached to an inside surface of stent 12 with fastening elements 18 projecting through stent 12. However, instead of utilizing looped locking elements 24 as a means for securing fastening elements 18 to stent 12, a linear locking element 26 may be looped through each fastening element 18 and secured to the stent 12 independently of its connection to the fastening elements 18. More specifically, a linear locking element 26 may be threaded and looped through each fastening element 18 while remaining along an outside surface of stent 12. The end points of linear locking element 26 are secured to stent 12, thereby attaching graft 10 to stent 12.

Alternatively, a linear locking element 26 may be threaded through (not looped through) fastening elements 18 and secured to stent 12 at at least two points along a length of stent 12 (not shown). In other words, a linear locking element 26 may be threaded through fastening elements 18 while remaining along an outside surface of stent 12, with each end of linear locking element 26 knotted around an element 12A, 12B, 12C, or 12D of stent 12 to attach graft 10 to stent 12.

The shape of the fastening elements 18 is not limited to a D-shaped ring, as illustrated in FIG. 4. Alternatively, fastening elements 18 may be round, square, triangular, or any other shape suitable for engagement with locking elements by which the graft 10, through its fastening elements 18, is secured to a stent 12 which surrounds it.

A further embodiment of the present invention includes a plurality of fastening elements, which are an integral part of outer layer 16, extending outwardly from outer layer 16 disposed along the length and/or circumference of outer layer 16 of tubular graft 10. In other words, each fastening element is not a distinct component from outer layer 16 as illustrated in FIG. 4. Instead, the fastening elements are part of the material of outer layer 16, i.e., loosely knitted, woven, or braided strands of material that form loops to act as fastening elements. At least some of the fastening elements are adapted to be secured on outer surface 20 of stent 12 surrounding graft 10. The configurations of this embodiment with respect to means for securing the fastening elements to stent 12 (i.e., looped locking elements 24 or a linear locking element 26) are essentially the same as those of the embodiment of graft 10 comprising fastening elements 18 described previously herein with reference to FIGS. 1-3.

An exemplary material for forming inner layer 14 of graft 10 is expanded polytetrafluoroethylene. The present invention, however, is not limited to polytetrafluoroethylene, and may include any material that offers the desired non-porous property of inner layer 14. The material of outer layer 16 may be a woven or knit polyester. The present invention, however, is not limited to polyester, and may include any knitted, woven, or braided material suitable for lamination to inner layer 14. Furthermore, the material of outer layer 16 is not limited to one that is porous, and may include any non-porous material suitable for lamination to inner layer 14.

Fastening elements 18 and/or locking elements 26 may comprise conventional suture material. Other materials may be used as well, however, and may comprise, for example, wire or plastic. One or both of the fastening element material and the locking element material may comprise, in whole or in part, a radiographically differentiable material.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The invention claimed is:

1. A non-porous stent-graft comprising:
   a graft comprising:
      an inner layer of a non-porous material;
      an outer layer of material laminated to said inner layer; and
      a fastening element adapted to be secured to said stent, wherein said fastening element is fixed between said inner layer and said outer layer, and wherein said fastening element comprises a closed loop penetrating through said outer layer in no more than two locations;
   a stent disposed around an exterior portion of the graft; and
   a locking element coupled to the stent and to the fastening element of the graft, wherein the locking element does not pass through the graft.

2. The stent-graft as recited in claim 1 comprising a plurality of said fastening elements distributed lengthwise and/or circumferentially on said graft.

3. The stent-graft as recited in claim 1, wherein said fastening elements comprise D-shaped rings.

4. The stent-graft as recited in claim 1, wherein the material of said inner layer is expanded polytetrafluoroethylene.

5. The stent-graft as recited in claim 1, wherein the material of said outer layer is polyester.

6. The stent-graft as recited in claim 1, wherein the material of said outer layer is knitted, woven, or braided.

7. The stent-graft as recited in claim 1, wherein the material of said fastening elements is a radiographically differentiable material.

8. A stent-graft comprising:
   a stent disposed around an exterior portion of a graft said graft comprising:
      an inner layer of a non-porous material; and
      an outer layer of knitted, woven, or braided material laminated to said inner layer, wherein said outer layer includes a plurality of fastening elements extending outwardly from said outer layer along a length of said outer layer of said tubular graft, wherein each of the plurality of fastening elements comprises a closed loop penetrating through-said outer layer in no more than two locations, at least some of said fastening elements positioned to extend between elements of the stent when said stent is surrounding said graft; and;
   a locking element coupled to the stent and to the fastening element of the graft, wherein the locking element does not pass through the graft.

9. The stent-graft as recited in claim 8, wherein said fastening elements comprise D-shaped rings.

10. The stent-graft as recited in claim 8, wherein the material of said inner layer is expanded polytetrafluoroethylene.

11. The stent-graft as recited in claim 8, wherein the material of said outer layer is polyester.

12. A stent-graft for defining a fluid passageway in a body lumen, said stent-graft comprising:
   a stent; and a graft, said graft comprising:
  an inner layer of a non-porous material;
  an outer layer of knitted, woven, or braided material laminated to said inner layer; and
  a plurality of fastening elements, wherein at least a part of each fastening element is fixed between said inner layer and said outer layers and wherein each of the plurality of fastening elements comprises a closed loop penetrating through said outer layer in no more than two locations;
  said stent surrounding said graft and having a plurality of stent elements, each of said plurality of fastening elements projecting into a space defined between the stent elements and entirely within said space, said fastening elements being secured to said stent.

13. The stent-graft as recited in claim 12, wherein said fastening elements comprise D-shaped rings.

14. A stent-graft for defining a fluid passageway in a body lumen, said stent-graft comprising:
  a stent; and
  a graft, said graft comprising;
    an inner layer of a non-porous material;
    an outer layer of knitted, woven, or braided material laminated to said inner layer; and
    a plurality of fastening elements, wherein at least a part of each fastening element is fixed between said inner layer and said outer layers and wherein each of the plurality of fastening elements comprises a closed loop penetrating through said outer layer in no more than two locations;
    said stent surrounding said graft and secured thereto through said fastening elements, wherein said graft is attached to said stent with said fastening elements projecting through said stent and a plurality of looped locking elements securing said fastening elements to said stent.

15. The stent-graft as recited in claim 14, wherein the material of said looped locking elements is a radiographically differentiable material.

16. A stent-graft for defining a fluid passageway in a body lumen, said stent-graft comprising:
  a stent comprising stent elements; and
  a graft, said graft comprising;
    an inner layer of a non-porous material; and
    an outer layer of knitted, woven, or braided material laminated to said inner layer, wherein said outer layer includes a plurality of fastening elements extending outwardly from said outer layer along a length of said outer layer of said graft, at least some of said fastening elements adapted to be secured on an outer surface of the stent surrounding said graft, at least a part of each said fastening element being disposed between said inner layer and said outer layer and extending into a space between said stent elements, wherein each of the plurality of fastening elements comprises a closed loop penetrating through said outer layer in no more than two locations; and
  a locking element coupled to the stent and to at least one of the fastening elements of the graft.

17. A stent-graft for defining a fluid passageway in a body lumen, said stent-graft comprising:
  a stent; and
  a graft, said graft comprising;
    an inner layer of a non-porous material; and
    an outer layer of knitted, woven, or braided material laminated to said inner layer, wherein said outer layer includes a plurality of fastening elements extending outwardly from said outer layer along a length of said outer layer of said graft, at least some of said fastening elements adapted to be secured on an outer surface of the stent surrounding said graft, at least a part of each said fastening element being disposed between said inner layer and said outer layer, wherein each of the plurality of fastening elements comprises a closed loop penetrating through said outer layer in no more than two locations, wherein said graft is attached to said stent with said fastening elements projecting through said stent and a plurality of looped locking elements secured to said stent by knotted loops of suture material.

* * * * *